(12) United States Patent
Viswanathan et al.

(10) Patent No.: US 7,527,725 B2
(45) Date of Patent: May 5, 2009

(54) UPGRADING DRIP OIL

(75) Inventors: Krishnan Viswanathan, Houston, TX (US); Lau S. Yang, Wilmington, DE (US); Ellen S. Lenz, West Chester, PA (US); David W. Leyshon, West Chester, PA (US)

(73) Assignees: Equistar Chemicals, LP, Houston, TX (US); Lyondell Chemical Technology, L.P., Greenville, DE (US)

( * ) Notice: Subject to any disclaimer, the term of this patent is extended or adjusted under 35 U.S.C. 154(b) by 496 days.

(21) Appl. No.: 11/407,739

(22) Filed: Apr. 20, 2006

(65) Prior Publication Data

US 2007/0249886 A1    Oct. 25, 2007

(51) Int. Cl.
*C10G 7/00*    (2006.01)
*C07C 7/04*    (2006.01)
*C07C 13/61*   (2006.01)

(52) U.S. Cl. .......... 208/347; 585/809; 585/810
(58) Field of Classification Search ............ 208/347, 208/354; 585/803, 802, 804, 809, 810
See application file for complete search history.

(56) References Cited

U.S. PATENT DOCUMENTS

| 3,860,498 A | * | 1/1975 | Jones ................ 205/784 |
| 3,927,135 A | * | 12/1975 | Suggitt et al. ........ 585/302 |
| 6,258,989 B1 | * | 7/2001 | Owen et al. .......... 585/318 |

FOREIGN PATENT DOCUMENTS

DE           238038 A    *    8/1986

\* cited by examiner

*Primary Examiner*—Walter D Griffin
*Assistant Examiner*—Renee Robinson
(74) *Attorney, Agent, or Firm*—Roderick W. MacDonald

(57) ABSTRACT

A method is disclosed for upgrading drip oil comprising subjecting the drip oil to multiple distillation steps to form a stream rich in aromatics and a separate stream rich in dicyclopentadiene.

5 Claims, 1 Drawing Sheet

UPGRADING DRIP OIL

FIELD OF THE INVENTION

This invention relates to the thermal cracking of hydrocarbons, more specifically to the cracking of normally gaseous hydrocarbons such as ethane and propane, and the recovery of products from the cracked product. In particular, this invention relates to the upgrading of the cracked product known as drip oil to higher value final products of the cracking process.

DESCRIPTION OF THE PRIOR ART

Thermal cracking of hydrocarbons is a petrochemical process that is widely used to produce olefins such as ethylene, propylene, butenes, butadiene, and aromatics such as benzene, toluene, and xylenes. In an olefin production plant, a hydro carbonaceous feedstock such as ethane, propane, naphtha, gas oil, or other fractions of whole crude oil is mixed with steam which serves as a diluent to keep the hydrocarbon molecules separated. This mixture, after preheating, is subjected to severe hydrocarbon thermal cracking at elevated temperatures from about 1,450 to about 1,550 degrees Fahrenheit (° F.) in a pyrolysis furnace (thermal cracker or cracker).

The cracked product effluent (cracked product) of the pyrolysis furnace contains hot, gaseous hydrocarbons of great variety from 1 to 35 carbon atoms per molecule ($C_1$-$C_{35}$, inclusive), and includes saturated and unsaturated paraffins (aliphatics) and saturated and unsaturated cyclic paraffins including alicyclics and aromatics, but little, if any, heterocyclics. This product is then subjected to further processing to produce, as products of the olefin plant, individual streams of molecular hydrogen, ethylene, and propylene. After separation of these individual product streams, the remaining cracked product contains essentially hydrocarbons with four carbon atoms per molecule ($C_4$) and heavier. This remainder is fed to a debutanizer wherein a crude $C_4$ stream is separated as overhead while a $C_5$ and heavier stream is removed as a bottoms product.

When cracking gaseous ethane, ethylene forms from cracking two carbon-hydrogen bonds on the ethane molecule. Methane can also be formed when the carbon-carbon bond is cleaved, and the resulting methyl radicals pick up hydrogen radicals. Acetylene and hydrogen can also be formed, but when run correctly, an ethane cracker yields a cracked product that is predominantly ethylene.

When cracking gaseous propane, propylene as well as ethylene is formed, along with some methane and ethane if the carbon-carbon bond of propane is cleaved. A well run propane cracker will produce a cracked product that is predominantly propylene and ethylene. Mixtures of ethane and propane are also cracked with similar results.

When cracking normally gaseous hydrocarbons such as ethane and/or propane, a minor, but significant amount of liquid hydrocarbons of a heavier molecular weight ($C_5$ to $C_{11}$ and heavier with traces of $C_4$ saturates and olefins and $C_3$ olefins, typically $C_6$ to $C_{12}$) are normally recovered from the cracked furnace product before that product is processed for recovery of its olefin content. This liquid is most often termed "drip oil." It contains paraffins, and cycloparaffins (alicyclic and aromatic), both saturated and unsaturated. Drip oil typically boils in the gasoline range of from about 100 to about 400° F.

Heretofore, drip oil has been processed to separate out a $C_8$ to $C_{10}$ "resin oil" containing saturated and unsaturated paraffins and cyclic paraffins including alicyclics (aliphatic cyclics) and aromatics. This resin oil is sent directly to the automotive gasoline pool.

Cyclopentadiene (CPD, $C_5H_6$) is present in drip oil. Dicyclopentadiene (DCPD, $C_{10}H_{12}$) and related dimers thereof form spontaneously in drip oil under mild condition upon storage (e.g., temperature of 20-120° F.).

CPD and DCPD are well established chemical building blocks. DCPD is the more stable of the two compounds, and, therefore, the more available form in industry. Although both CPD and DCPD are used commercially, the CPD monomer obtained by thermally cracking DCPD dimer has extensive use owing to its versatility and reactive conjugated diolefin arrangement. DCPD (4, 7-methano-3α-tetrahydroindene) is the form in which CPD is typically marketed commercially. DCPD exists in two stereo isomeric forms, the endo- and exo-isomers, and both are included herein in the term DCPD.

CPD, with its two conjugated double bonds and an active methylene group, can undergo a diene addition reaction with almost any unsaturated compound, hence its versatility. CPD polymerizes spontaneously at ordinary temperatures and pressures to DCPD, and to other oligomers such as trimers and co-dimers. CPD boils at about 106.7° F. DCPD boils at about 338° F. which is also essentially its thermal cracking temperature at atmospheric pressure. As DCPD boils in a simple fractional distillation column, the overhead temperature of that column can be maintained at about 105° F. to about 107° F. to yield an essentially pure CPD monomer distillate. Since this monomer dimerizes spontaneously, it is used promptly, or it must be stored at a low temperature, e.g., sub zero ° F., to avoid the need for re-cracking.

Therefore, a DCPD product is of value in industry, and, as will be discussed later, can have a wide variety of uses of greater value than as an addition to the automotive gasoline pool.

SUMMARY OF THE INVENTION

In accordance with this invention, drip oil is upgraded by multiple fractional distillation steps to form a stream that contains aromatics and is useful in the automotive gasoline pool or other applications such as the aromatic resin market, and a separate stream that contains a high concentration of DCPD which is of use and value separately and independently of the automotive gasoline pool.

BRIEF DESCRIPTION OF THE DRAWING

The sole FIGURE.

DETAILED DESCRIPTION OF THE INVENTION

Figure 1:
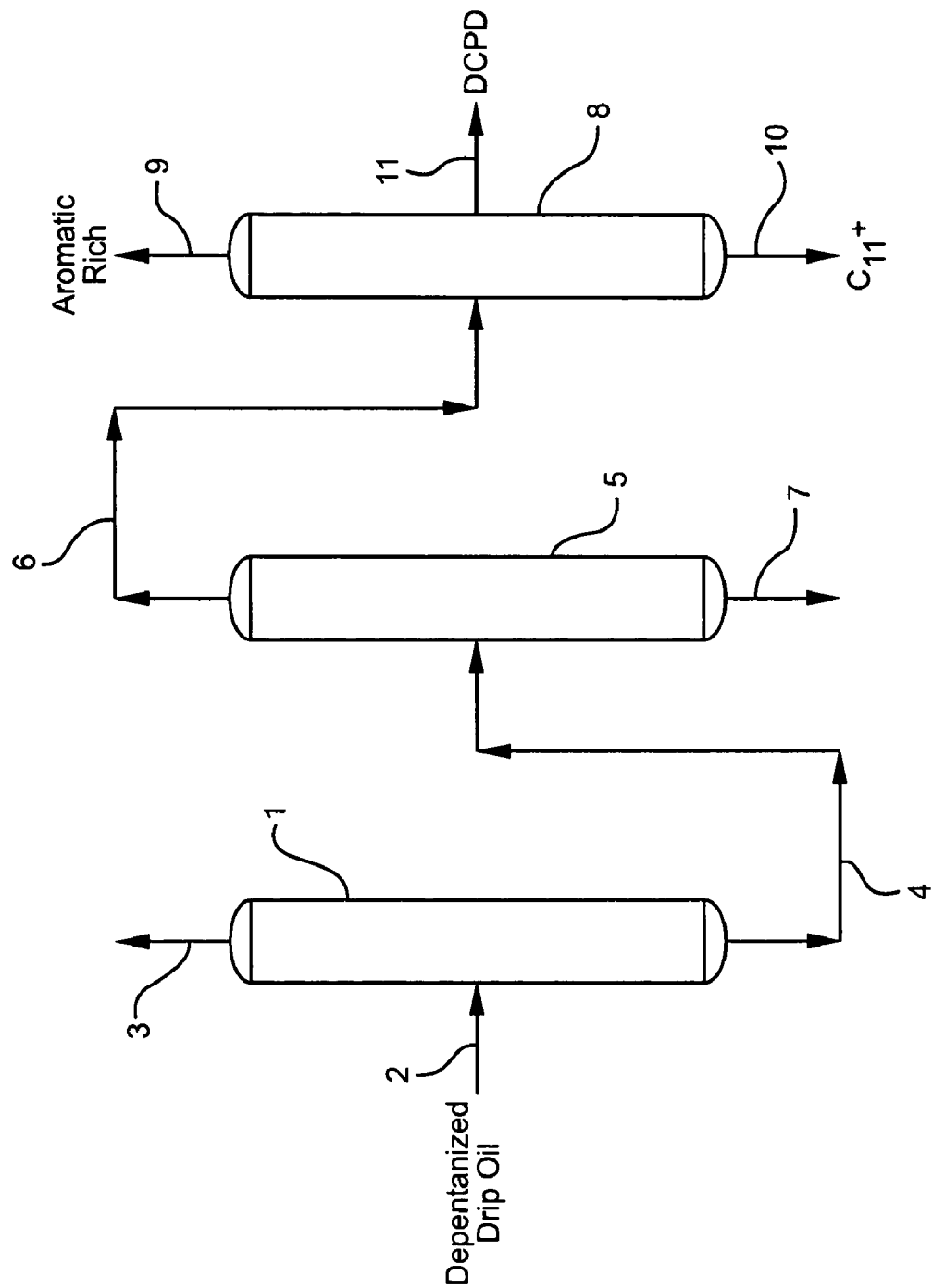
FIG. 1, shows one processing embodiment for upgrading drip oil pursuant to this invention.

FIG. 1 shows a first re-boiled fractional distillation column (tower) 1 which employs a drip oil feedstock 2 to produce a first overhead stream 3, and a first bottoms stream 4. Tower 1, like the other towers in FIG. 1, employs a conventional reflux loop on its overhead stream, which loop is not shown for sake of clarity and brevity. Tower 1 can be operated at a temperature of from about 100 to about 250° F. at a pressure of from about 5 to about 150 psig.

Stream 3 contains $C_5$ to $C_7$ hydrocarbons while stream 4 contains $C_8$ to $C_{10}$, inclusive, hydrocarbons. Both streams 3 and 4 contain primarily saturated and unsaturated paraffins and cycloparaffins including alicyclics and aromatics.

Stream 3 is removed from the process of this invention for other processing such as selective hydrogenation and solvent extraction of aromatics, while stream 4 is passed as feed to second re-boiled fractional distillation column 5. In tower 5, stream 4 is split into a second overhead stream 6, and a second bottoms stream 7. Tower 5 can be operated at a temperature of from about 120 to about 300° F. at a pressure of from about 0.5 to about 4 psig.

Stream 7 is essentially $C_{11}$ and heavier materials, essentially paraffinic and cycloparffinic, and is removed from this process for other processing elsewhere in the olefin plant, e.g., hydrotreating.

Stream 6 (resin oil) contains $C_8$ to $C_{10}$ hydrocarbons, inclusive (essentially saturated and unsaturated paraffins and cycloparaffins including alicyclics and aromatics), and can contain a major amount of DCPD and related oligomers such as co-dimers of CPD with one or more of methylcyclopentadiene, isoprene, and piperylene. Other oligomers can be present such as dimers of isoprene and co-dimers of isoprene and cyclopentene. As used in this disclosure, the term "major amount" means equal to or greater than 50 weight percent (wt. %), and "minor amount" means less than 50 wt. %, both based on the total weight of the material in question.

Overhead stream 6 is passed to third re-boiled fractional distillation column 8. In tower 8, stream 6 is distilled into a third overhead stream 9, a third bottoms stream 10, and a first side stream 11. Tower 8 can be operated at a temperature of from about 120 to about 300° F. at a pressure of from about 0.5 to about 8 psig.

Stream 9 is rich in aromatics and can contain a major amount of aromatics. It also contains $C_8$ to $C_{10}$ hydrocarbons, inclusive, (essentially saturated and unsaturated paraffins and cycloparaffins including alicyclics and aromatics). Stream 9 is removed from the process for processing elsewhere in the olefin plant, i.e., for addition to the automotive gasoline pool. It could also be sold to and used in the aromatic resin industry.

Stream 10 contains $C_{11}$ and heavier hydrocarbons (essentially saturated and unsaturated paraffins and cycloparaffins including alicyclics and aromatics) and is removed from the process for processing elsewhere in the olefin plant, e.g., hydrotreating.

Stream 11 contains a substantial, e.g., major, amount of a mixture of DCPD and CPD co-dimers. This stream can contain at least about 65 wt. % DCPD; and at least about 5 wt. % of a mixture of isoprene dimer, co-dimers of one or more of CPD and isoprene, CPD and piperylene, and isoprene and cyclopentene; all wt. % based on the total weight of the stream.

Stream 11 is of value in the resin industry, e.g., for making unsaturated polyester resins, and the like, and, as such, is of higher value than as an addition to the automotive gasoline pool.

EXAMPLE 1

Distillation of Resin Oil

In the process shown in FIG. 1, tower 1 is fed a depentanized drip oil 2 that consists essentially of about 27 wt. % $C_5$ to $C_8$, inclusive, saturated and unsaturated straight chain paraffins and alicyclic paraffins, about 58 wt. % $C_6$ to $C_8$, inclusive, aromatics and ethyl benzene, and about 13 wt. % $C_9$ and $C_{10}$ olefins and diolefins, the remainder being $C_{11}$ and heavier paraffins and cycloparaffins, both saturated and unsaturated, all wt. % based on the total weight of feed 2.

Feed 2 at a temperature of about 300° F. is passed into tower 1 at the rate of about 150,000 pounds per hour (pph). Tower 1 has a bottom temperature of about 300° F. at 10 psig, and distills feed 2 into an overhead 3 containing $C_6$ and $C_7$ paraffins and cycloparaffins, saturated and unsaturated; and a bottoms 4 consists essentially of $C_8$ to $C_{10}$, inclusive, saturated and unsaturated paraffins and cycloparaffins, including alicyclics and aromatics.

Stream 4 is passed to tower 5 at a rate of about 35,000 pph. Tower 5 has a bottom temperature of about 280° F. at about 120 mmHg, and distills stream 4 into overhead stream 6, and bottoms stream 7. Stream 7 contains $C_{11}$ and heavier hydrocarbons, both saturated and unsaturated.

Stream 6 (resin oil) consists essentially of about 40 wt. % DCPD, about 10 wt. % co-dimer of CPD and methylcyclopentadiene (MCPD), about 1.5 wt. % dimer of MCPD, about 1.5 wt. % dimer of isoprene, about 10 wt. % co-dimer of isoprene and CPD, less than 1 wt. % co-dimer of CPD and piperylene, less than 0.5 wt. % co-dimer of isoprene and cyclopentene, and about 1.5 wt. % trimers of isoprene, CPD, and piperylene, with the remainder being indene, naphthalene and the like, including small amounts of benzene and styrene, all wt. % based on the total weight of stream 6.

Stream 6 is passed at the rate of about 30,000 pph to tower 8 which is operated at a bottom temperature of about 290° F. at 80 mmHg. Tower 8 distills stream 6 into overhead 9, bottoms 10 and side stream 11. Stream 9 contains $C_8$ to $C_{10}$, inclusive, hydrocarbons consisting essentially of saturated and unsaturated paraffins and cyclicparaffins including alicyclics and aromatics. Stream 9 contains at least about 50 wt. % $C_8$ to $C_{10}$, inclusive, aromatics based on the total weight of stream 9. Stream 10 contains $C_{11}$ and heavier hydrocarbons, both saturated and unsaturated.

Stream 11 is recovered at the rate of about 20,000 pph. Stream 11 contains about 91 wt. % of a mixture of DCPD; isoprene dimer; co-dimers of isoprene and CPD, piperylene and CPD, and isoprene and cyclopentene; and trimers of isoprene, CPD, and piperylene. Of this mixture, the majority component is DCPD. The remaining about 9 wt. % consists essentially of $C_8$ to $C_{11}$, inclusive, paraffins and cycloparaffins, both saturated and unsaturated. Stream 11 contains at least about 65 wt. % DCPD and at least about 5 wt. % of a mixture of isoprene dimer, and co-dimers of at least one of isoprene and CPD, piperylene and CPD, and isoprene and cyclopentene. All wt. % are based on the total weight of stream 11. This stream is useful in making polyester resins.

EXAMPLE 2

Batch Distillation of Resin Oil

A sample of resin oil (Stream 6 in Example 1) is analyzed by Gas Chromatography (GC). Results are shown in Table 1. Batch distillation of the resin oil at 50 mmHg produces a heavy fraction (about 60 wt. % of the total) and a light fraction (about 40 wt. % of total). The main components in these fractions and their concentrations are shown in Table 1.

TABLE 1

Batch Distillation of Resin Oil

| Component | Resin Oil (wt. %) | Light Fraction (wt. %) | Heavy Fraction (wt. %) |
|---|---|---|---|
| Cyclopentene | 0.30 | 0.02 | 0.02 |
| Toluene | 5.3 | 10.3 | 0.001 |
| Xylenes | 26.2 | 55.0 | 5.3 |
| Vinyl norbonene | 1.2 | 2.5 | 0.2 |
| Styrene | 15.8 | 26.9 | 6.7 |
| CPD-piperylene Dimers | 4.4 | 0.4 | 7.2 |
| CPD-isoprene Dimers | 6.2 | 0.3 | 10.9 |
| Exo-DCPD | 0.52 | 0.06 | 0.9 |
| Endo-DCPD | 40.0 | 4.5 | 68.7 |

EXAMPLE 3

DCPD Based Unsaturated Polyester Resin

An unsaturated polyester resin (UPR) is synthesized using the heavy fraction from Example 2. To a 1-L reactor are added 228 g of maleic anhydride and 29.2 g of water. The mixture is heated to 110° C., and 224 g of the heavy fraction prepared in Example 1 is introduced through a dropping funnel while the reaction temperature is kept below 130° C. The mixture is kept at 135° C. for 2 h after the addition, then 219 g of diethylene glycol is added. The temperature is raised to 210° C. and kept at 210° C. for 5 h until the acid number drops to 39 mg KOH/g. About 0.07 g of hydroquinone is added and the reaction mixture is cooled. Styrene is blended to give a product containing 35 wt. % styrene with a viscosity of 270 cps.

The resin solution is cured with 1 wt. % of methyl ethyl ketone peroxide and 0.1 wt. % of cobalt naphthenate in a glass mold. The physical properties of the cured sample are compared with those of a regular commercial DCPD UPR resin in Table 2. It shows that the resin made from the heavy fraction is very similar to a commercially available regular DCPD based UPR resin.

TABLE 2

Comparison of UPR Resins

| | Regular Commercial DCPD UPR resin | Resin of Example 3 |
|---|---|---|
| Viscosity at 35% styrene, cps | 300 | 270 |
| Tensile strength, psi | 6500 | 6500 |
| Tensile elongation, % | 1.5 | 1.8 |
| Tensile modulus, kpsi | 480 | 500 |
| Flex strength, psi | 15000 | 16000 |
| Flex modulus, kpsi | 450 | 490 |
| DTUL, ° C. | 75 | 70 |
| Barcol hardness | 40 | 40 |

We claim:

1. A method for upgrading drip oil comprising subjecting said drip oil to a first fractional distillation to form a first overhead stream containing $C_6$ and $C_7$ hydrocarbons and a first bottoms stream containing $C_8$ and heavier hydrocarbons, subjecting said first bottoms stream to a second fractional distillation to form a second overhead stream containing $C_8$ to $C_{10}$, inclusive, hydrocarbons and a second bottoms stream containing $C_{11}$ and heavier hydrocarbons, subjecting said second overhead stream to a third fractional distillation to form a third overhead stream containing $C_8$ to $C_{10}$, inclusive, hydrocarbons which is aromatic rich, a third bottoms stream which contains $C_{11}$ and heavier hydrocarbons, and a first side stream that contains substantial amounts of dicyclopentadiene.

2. The method of claim 1 wherein said drip oil consists essentially of $C_5$ to $C_{12}$, inclusive, paraffins and cycloparaffins including alicyclics and aromatics, and boils in the range of from about 100 to about 420° F.

3. The method of claim 1 wherein said first overhead and said first bottoms streams consist essentially of saturated and unsaturated paraffins and cycloparaffins including alicyclics and aromatics, said second overhead stream contains a major amount of dicyclopentadiene and co-dimers of cyclopentadiene, said third overhead stream contains a major amount of aromatics, and said first side stream contains a major amount of dicyclopentadiene and co-dimers of cyclopentadiene.

4. The method of claim 3 wherein said first side stream contains at least about 75 wt. % dicyclopentadiene; and at least about 5 wt. % of a mixture of isoprene dimer, and co-dimers of isoprene and cyclopentadiene, piperylene and cyclopentadiene, and isoprene and cyclopentene; all wt. % based on the total weight of said first side stream.

5. The method of claim 1 wherein said first distillation is conducted at a temperature of from about 100 to about 250° F. at a pressure of from about 5 to about 150 psig, said second distillation is conducted at a temperature of from about 120 to about 300° F. at a pressure of from about 0.5 to about 4 psig, and said third distillation is conducted at a temperature of from about 20 to about 300° F. at a pressure of from about 0.5 to about 8 psig.

* * * * *